US005907080A

United States Patent [19]
Karatzas et al.

[11] Patent Number: 5,907,080
[45] Date of Patent: May 25, 1999

[54] METHOD FOR DEVELOPMENT OF TRANSGENIC DWARF GOATS

[75] Inventors: Costas Karatzas; Carol Keefer; Jeffrey D. Turner, all of Quebec, Canada

[73] Assignee: Nexia Biotechnologies, Inc., Ste. Anne de Bellevue, Canada

[21] Appl. No.: 08/565,057

[22] Filed: Nov. 30, 1995

[51] Int. Cl.⁶ .......................... C12N 15/00; C12N 15/09; C12N 15/63; C12N 5/00
[52] U.S. Cl. .................. 800/25; 800/21; 800/22; 800/23; 800/14; 800/7; 435/455
[58] Field of Search ................ 435/172.3, 455; 800/2, 25, 22, 23, 21, 14, 7

[56] References Cited

U.S. PATENT DOCUMENTS

| | | | |
|---|---|---|---|
| 4,873,316 | 10/1989 | Meade et al. | 530/412 |
| 4,994,384 | 2/1991 | Prather et al. | 435/172.2 |
| 5,057,420 | 10/1991 | Massey | 435/172.2 |
| 5,304,489 | 4/1994 | Rosen | 435/320.1 |
| 5,322,775 | 6/1994 | Clark et al. | 435/69.1 |

FOREIGN PATENT DOCUMENTS

| | | | |
|---|---|---|---|
| A2 0247494 | 12/1987 | European Pat. Off. | |
| A2 0350052 | 1/1990 | European Pat. Off. | |
| WO 89/01972 | 3/1989 | WIPO | |
| WO 90/03432 | 4/1990 | WIPO | C12N 5/06 |
| WO 90/10699 | 9/1990 | WIPO | |
| WO 92/22644 | 12/1992 | WIPO | C12N 15/00 |
| WO 93/03164 | 2/1993 | WIPO | C12N 15/90 |
| WO 93/04165 | 3/1993 | WIPO | C12N 15/00 |
| WO 93/25567 | 12/1993 | WIPO | C12N 5/06 |
| WO 93/25669 | 12/1993 | WIPO | C12N 9/20 |
| WO 94/21111 | 9/1994 | WIPO | A01K 67/027 |
| WO 94/25586 | 11/1994 | WIPO | C12N 15/00 |
| WO 94/26884 | 11/1994 | WIPO | C12N 15/00 |
| WO 95/06716 | 3/1995 | WIPO | C12N 5/06 |
| WO 95/08625 | 3/1995 | WIPO | C12N 15/00 |
| IB96/01434 | 12/1997 | WIPO | |

OTHER PUBLICATIONS

Braun et al., "Non–surgical Embryo Collection in the Dairy Goat", Proc. of the Int'l Goat Production Symposium, *Dairy Goat Production,* 1990.
Wilmut et al. "Production of pharmaceutical proteins in milk", Experientia 47:905, 1991.
Keskintepe et al., "In Vitro development of morulae from immature caprine oocytes", Zygote 2:97, 1994.
Groenen et al., "Regulation of expression of milk protein genes:a review", Livestock Prod. Science 38:61, 1994.
Collas et al., "Nuclear Transplantation by Microinjection of Inner Cell Mass and Granulosa Cell Nuclei", Molecular Reproduction and Development 38:264–267, 1994.
Ebert et al., "Induction of Human Tissue Plasminogen Activator in the Mammary Gland of Transgenic Goats", Biotechnology 12:699–702, 1994.
Eistetter, H., "Pluripotent Embryonal Stem Cell Lines Can Be Established from Disaggregated Mouse Morulae", Develop. Growth & Differ. 31(3):275–282, 1989.
Eyestone, W.H., "Challenges and Progress in the Production of Transgenic Cattle", Reprod. Fertil. Dev. 6: 647–52, 1994.
Hall, A., "The Pygmy Goat in America with the Nigerian Dwarf", Hall Press, San Bernadino, CA, pp. 7–31, 74–75, and 126–140, 1982.
Pieper et al., "Efficient generation of functional transgenes by homologous recombination in murine zygotes" Nucleic Acids Research 20(6):1259–1264, 1992.
Pursel et al., "Status of Research with Trasgenic Farm Animals", J. Anim. Sci. 71(3):10–19, 1993.
Seidel Jr., G.E., "Resource Requirements for Transgenic Livestock Research", J. Anim. Sci. 71(3):26–33, 1993.
Simons et al., "Gene Transfer Into Sheep", Biotechnology 6:179–183, 1988.
Tatham et al., "Enucleation by Centrifugation of In Vitro–Matured Bovine Oocytes for Use in Nuclear Transfer", Biology of Reproduction 53:1088–1094, 1995.
Wheeler, M.B., "Development and Validation of Swine Embryonic Stem Cells: A Review", Reprod. Fertil. Dev. 6:563–568, 1994.
Youngs et al., "Embryo Transfer in Dairy Goats", Proceedings of Int. Goat Production Symposium, Florida A & M University, Tallahassee, FL., pp. 170–176, 1990.
Schikora et al. Beitrage Zur Tropischen Landwirtschaft and Veterinarmidizin. 30(4):463–70. abstract only, 1992.
Wilmut et al. New Scientist. vol. 7: 56–59 (1988).
Ebert et al. Bio/Technology. vol. 9: 835–838 (1991).
Hughes. AgBiotech News and Information vol. 3: No. 1: 25–28. (1991).
Bradley et al. Bio/Technology. vol. 10: 534–538 (1992).
Steer et al. Human Reproduction vol. 7: No. 1: 117–119. (1992).

*Primary Examiner*—Deborah Crouch
*Assistant Examiner*—Jill D. Martin
*Attorney, Agent, or Firm*—Clark & Elbing, LLP

[57] ABSTRACT

The invention features a method which includes the following steps: (a) introducing a transgene into a zygote of a dwarf goat, (b) transplanting the zygote into a pseudopregnant non-dwarf goat, and (c) allowing the zygote to develop to term. In another aspect the invention features a method which includes the following steps: (a) introducing a transgene into an embryo of a dwarf goat, (b) transplanting the embryo into a pseudopregnant non-dwarf goat, and (c) allowing the embryo to develop to term.

6 Claims, No Drawings

METHOD FOR DEVELOPMENT OF TRANSGENIC DWARF GOATS

FIELD OF THE INVENTION

The field of the invention is methods for development of transgenic goats.

BACKGROUND OF THE INVENTION

Selective breeding of domesticated animals, based on phenotypic traits, has led to significant genetic improvement in a variety of breeds. For example, selective breeding techniques have resulted the production of diary cows which produce more milk and produce milk having improved fat and protein profiles. Reproductive technologies including artificial insemination and embryo transfer (i.e., transferring an embryo to an animal that did not produce it) have contributed to this genetic improvement. Advanced reproductive and molecular technologies, e.g., embryo cloning, and marker assisted selection (genetic screening), allow even greater control over the selection of desirable traits. However, these practices only allow selection and propagation of traits which are already in the gene pool of the species. In order to replace or modify existing genes or insert genes for traits which are not present in the gene pool of the species, a transgene must be introduced into the animal. Transgenes can be used to introduce disease resistance, alter the composition of animal derived products (milk, serum, etc.), produce pharmaceutical or nutriceuticals, or for other purposes.

A number of techniques can be used to create transgenic animals. Among the techniques which have been successfully used are: pronuclear injection of the transgene, nuclear transplantation, and injection of genetically altered stem cells into host embryos (chimera production).

Pronuclear injection is a commonly used procedure for germ line insertion of genes. While this technique is attractive because it can be used successfully with a range of animals, the inability to control integration of the transgene and the large number of ova which must be injected to obtain even a single transgenic offspring combine to make the technique rather inefficient, at least for animals other than mice. Moreover, animals which are deemed transgenic, e.g., by Southern analysis, may be mosaic, may contain the transgene but not express it, may express it in an undesirable manner, or may express correctly but fail to transmit it to offspring. Despite these difficulties, transgenic mice, sheep, goats, cattle and pigs have been produced using pronuclear injection.

Transgenic mice have been created by genetically manipulating murine embryonic stem cells (ESC), e.g., by injecting a transgene into the ESC, and then injecting the altered embryonic stem cells into a host embryo. The resulting mice are mosaics in which genetically altered cells contribute to a greater or lesser extent to the somatic and germ cells.

Nuclear transfer is a third approach to the generation of transgenic animals. In this technique the nucleus of a donor cell is introduced into a recipient oocyte. Offspring have also been reported in the bovine and sheep from cultured inner cell mass (ICM) cells and embryonic disks, respectively, using the technique of nuclear transfer.

Embryo transfer is a technique in which an embryo taken from a donor animal is transferred to a recipient animal who brings the embryo to term. Embryo transfer has successfully produced offspring when embryos from dwarf goats were transferred into standard goats Sugie et al., 1970.

SUMMARY OF THE INVENTION

The invention features a method which includes the following steps: (a) introducing a transgene into a zygote of a dwarf goat, (b) transplanting the zygote into a pseudopregnant non-dwarf goat, and (c) allowing the zygote to develop to term. In another aspect the invention features a method which includes the following steps: (a) introducing a transgene into an embryo of a dwarf goat, (b) transplanting the embryo into a pseudopregnant non-dwarf goat, and (c) allowing the embryo to develop to term.

In another aspect, the invention features a method which includes the following steps (a) introducing a transgene into an zygote of a dwarf goat, (b) transplanting the zygote into a pseudopregnant dwarf goat, and (c) allowing the zygote to develop to term. In another aspect, the invention features a method which includes the following steps: (a) introducing a transgene into an embryo of a dwarf goat, (b) transplanting the embryo into a pseudopregnant dwarf goat, and (c) allowing the embryo to develop to term.

In preferred embodiments the method also includes: (d) breeding the offspring to produce a transgenic dwarf goat. In other preferred embodiments the introducing of the transgene into the embryo is by introducing an embryonic stem cell containing the transgene into the embryo; the introducing of the transgene into the embryo is by infecting the embryo with a retrovirus containing the transgene; the introducing of the transgene into the zygote is by injecting the pronucleus of the zygote with the transgene.

In other preferred embodiments at least four zygotes are transplanted into the pseudopregnant non-dwarf goat and at least four embryos are transplanted into the pseudopregnant non-dwarf goat.

In another aspect the invention features dwarf goat embryonic stem cells.

By "transgene" is meant a DNA sequence introduced into the germiline of non-human animal by way of human intervention such as by any of the methods described herein.

By "dwarf goat" is meant a Nigerian Dwarf goat or a Pygmy goat or any other goat of small size comparable to that of a Nigerian Dwarf goat or a Pygmy goat. Suitable goat breeds preferably weigh approximately 80 lbs or less at maturity and weigh 2.0 kg, more preferably 1.7, or 1.5 kg at birth. Suitable breeds are of a fetal size and neonatal size which permit a non-dwarf goat (i.e., a standard goat) to which the dwarf goat embryo or zygote are transferred to bear 3 or 4, more preferably 5 or 6, dwarf goats in a single pregnancy. Achondroplastic dwarf goats are suitable for use in the method of the invention as are dwarf goats whose small stature is due to some other cause.

Because several dwarf goat embryos can be implanted in a single pseudo-pregnant standard goat, the method of the invention provides a means by which to decrease the number of recipient animals required for the production of transgenic goats. Transfer of multiple dwarf embryos to standard goats as recipients results in an increase (e.g., 2- to 4-fold) in the number of offspring per recipient, compared to the implantation of standard goat embryos into standard goat recipients. This represents a significant increase in production efficiency and a significant decrease in cost of recipient animals compared to other systems, such as the transfer of standard goat embryos to standard goat recipients. Moreover, dwarf goats have characteristics, including lack of seasonality, early onset of sexual maturity, and small fetal and neonatal size, and good milk yield, which are highly desirable in transgenic animals used for the production of pharmaceuticals or nutriceuticals in milk. Lack of seasonality and early onset of sexual maturity decrease the generation interval as compared to other dairy ruminants. Using the method of the invention, a heterologous gene product can be expressed in the milk of a transgenic animal within a time-frame which is the shortest of any dairy ruminant (e.g., a year before that of transgenic dairy cattle).

It is the small fetal and neonatal size of dwarf goats which allows for the implantation of several embryos into a single standard goat recipient. Dwarf goats are a desirable system for the production of transgenic goats even when dwarf, rather than standard, goats are used as the recipient for embryos or zygotes. This is because a dwarf goats naturally produce more offspring in single pregnancy than do standard goats.

The method of the invention can be used with any method for producing transgenic dwarf goats, including: pronuclear injection (or any other means for introduction of a gene into a cell), nuclear replacement (embryo cloning), and injection of genetically-manipulated embryonic stem cells into embryos (chimera production). The method of the invention can also be used to develop other advanced reproductive and genetic technologies such as homologous recombination. The method of the invention has numerous advantages over other ruminant-based transgenic systems.

The method of the invention preferably entails expansion and propagation of dwarf goat progeny, transgenic (or otherwise genetically altered such that at some of the cells harbor a gene that does not naturally occur in the species) transfer of embryos or ova or zygotes to standard goat does. In general, 4 to 6 or more dwarf goat embryos can be transferred to a standard recipient doe using the method of the invention. This represents an significant improvement relative to the use of standard goats where only 1 or 2 standard goat offspring are born to a standard goat recipient.

Another aspect of the invention entails transfer of genetically manipulated dwarf goat embryos to dwarf goat does.

Other features and advantages of the invention will be apparent from the following description of the preferred embodiments thereof, and from the claims.

DESCRIPTION OF THE PREFERRED EMBODIMENTS

A. Dwarf Goats

Dwarf goats are indigenous to India, Arabia, China, West Indies and Africa (especially Nigeria, Ghana, and the Cameroons). Dwarf goats predominate in western Africa due to their natural resistance to the tse tse fly which destroys other goat types. This West African goat is also called the Fouta Djallon, Cameroon, Nigerian or tree goat.

Breeders in North America selecting for slightly different show traits have characterized two show breeds of Dwarf goats, the Pygmy goat and the Nigerian Dwarf goat. Nigerian Dwarves have slightly longer necks and legs and their barrels are not as wide or deep as those of Pygmies. Breeders of Pygmy goats also select for a more limited range of coat color. These show breeds are both derived from western African dwarf goats and have similar reproductive and milk production traits (Tables 2 and 3). Dwarf goats useful in the method of the invention include Nigerian Dwarf Goats, Pygmy Dwarf Goats, and other dwarf goats which are of a size which permit a standard goat to carry 3 or more to term in one gestation.

The American Nigerian Dwarf Goat Organization (Alvarado, Tex.; Internet Address: rivoire@abn.unt.edu) provides information concerning Nigerian Dwarf goats including breeder lists. According to the American Nigerian Dwarf Goat Organization, ideal does are 17" to 19" high (21" maximum), and ideal bucks are 19" to 20" high (23" maximum). Their ideal weight at maturity is 75 lbs. Of course, dwarf goats useful in the method the invention need not meet these stringent criteria. Nigerian Dwarf Goats average 2 lbs at birth. Bucks can reach sexual maturity at 7 weeks. Does can typically be breed at 7–8 months, although it is possible to breed them earlier. Nigerian Dwarf Goats are registerable with the American Goat Society, the International Diary Goat Registry, and the Canadian Goat Society. Additional Nigerian Dwarf Goat information is available on the Internet at http://www.okstate.edu/.../nigndwrf.html.

The National Pygmy Goat Association has set standard for the breed which have been accepted by the American Goat Society. According to these standards an adult buck is 16.0" to 23.6 high at the wither, and an adult doe is 16.0" to 22.4" high at the wither.

Information concerning both the Pygmy Goat and the Nigerian Dwarf Goat can be found in "The Pygmy Goat in America with the Nigerian Dwarf." (Alice Hall, Hall Press, San Bernardino, Calif., 1992; ISBN: 0-932218-13-X; Library of Congress Catalog Card Number: 82-90126).

The dwarf goats are homozygous for small size. Dwarfism appears to be controlled by three genes (Blanks, *A Morphological, Physiological and Genetic Investigation of the African Pygmy Goat*, Doctoral Thesis, Oregon State University, 1971). At birth, the typical dwarf kid is less than half the size of a standard kid at birth. Dwarf goat birth weights average 1.4 kg for females and 1.6 kg for males while for standard Saanens the birth weight are 3.6 kg for females and 3.8 kg for males. Hybrid dwarf-standard kids are intermediate between parental phenotypes.

TABLE 2

Comparison between Dwarf and Standard breed Goats

| Dwarf Goat (e.g., Pygmy, Nigerian) | Standard Goat (e.g., Saanen, Alpine) |
|---|---|
| Differences | |
| Breeds all year | Most are seasonal breeder (anestrous 4 months) |
| mature weight 20–35 kg (female) | mature weight 75 kg |
| sexually mature 3–6 months | sexually mature 10–12 months |
| Similarities | |
| gestation 5 months | gestation 5 months |
| milk production high (1000 lbs/yr) | milk production high (2700 lbs/yr) |
| twining, triplets typical | Singles, twinning typical |

Shorter Generation Times

Dwarf goats have a shorter generation time than other dairy ruminants (standard goats, sheep, cows) owing to their sexually precociousness. Dwarf goats of both sexes are mature rapidly. The females generally begin to cycle at two to six months of age, compared to nine months for standard goats, and are capable of carrying a pregnancy to term if impregnated at this time. Similarly, male Dwarf goats produce viable semen by two to three, compared to five months for standard goats. Standard management practice with Dwarf goats mandates that the males be removed from their litter mates by two months of age to prevent young bucks from mating with their sisters prior to weaning.

Early puberty is important because it allows a transgenic female to be impregnated at three to four months after birth, allowing for early milk production at kidding. The entire process beginning at microinjected ovum to lactating transgenic female is 14 months (five months for fetus gestation, four months for doe growth, and five months for doe gestation). Moreover, lactation can be induced hormonally, thus even further shortening the time required to obtain transgenic milk (five months for fetus gestation and two to four months for doe growth).

Lack of Seasonality

The Dwarf goat is sexually active throughout the year, a fact that further contributes to their shorter generation intervals. Standard goats in temperate climates have defined periods of sexual activity. In the northern hemisphere, standard goats have a defined rutting season from September to March with "heats" occurring some 18–21 days apart. in contrast, Dwarf goats are polyestrous (i.e., they do not show a period of sexual inactivity), probably because they evolved in the tropics where the seasonal effects on reproduction are slight. This lack of seasonality is an important aspect of Dwarf goat physiology because pubertal animals can be propagated year round either through natural breeding, superovulation, embryo transfer, or through frozen embryo storage with subsequent transfer. This is particularly advantageous for increasing numbers of transgenic animals. Some standard breeds of goats are less seasonally dependent than others and can be used as recipients throughout most of the year.

Lactational Performance

The lactational performance of transgenic Dwarf goats is sufficient to allow them to be a viable model for heterologous protein production. Typical lactation produces on average 1.0–1.5 L/day for 10 months, a remarkable amount considering the Dwarf goats' small body size. This lactation performance is thus sufficient to satisfy the requirement for gram quantities of protein. The American Goat Association has set production records for Pygmy goats as producing ⅓ of the larger dairy goat breeds. The International Dairy Goat Registry has set similar production standards for Pygmy and Nigerian dwarf goats. Although production standards are from 460 to 550 lbs (209 to 250 kg) for yearlings, older does may produce more. Does producing over 1,000 lbs (454 kg) with high butterfat (5.5%) and protein (4.2%) are not uncommon (*Dairy Goat journal*, 1993 and Nigerian Dwarf Goat Association). Recent evaluation of the milk of a Nigerian dwarf doe from our herd found average of 5.6% fat, 4.3% protein and 4.9% lactose (8 samples). This surpasses the standard goat average protein content of 3.0% for a Quebec dairy reporting lactational yields for 34 milking dairy goats (*Canadian Goat Society Quarterly*, November 1994).

TABLE 3

Production standards for yearling dwarf goats

| Association | Type | lbs per lactation (305 days) |
| --- | --- | --- |
| American Goat Association | pygmy | 500 |
| International Dairy Goat Registry | pygmy | 460 |
| | Nigerian dwarf | 550 |

(Hall, The Pygmy Goat in America, supra)

Small Physical Size

In addition to the advantages in production, the small physical size of Dwarf goats means that less space required to house lactating Dwarf does. In addition, their small size and personable nature also make handling the animals easier.

B. Multiple Birth Goat System

The multiple birth goat system is based on the use of dwarf goats. Because dwarf goat fetuses and neonates are small, a standard recipient doe can gestate and give birth to multiple Dwarf offspring successfully. Even dwarf does can successfully carry 3 to 4 dwarf goat offspring. Either approach results in increased multiplicity of offspring and shorter generation intervals compared to producing standard goats in standard goats. The method involves the collection of Dwarf goat embryos and their transfer into synchronized standard recipient goat does or into synchronized dwarf goat recipients. In one study we were able to recover a total of 67 dwarf goat embryos from six dwarf goat donors (average number embryos from each donor=11.2). In another study a total of 16 dwarf goat embryos were transferred to three standard goat recipients (average number embryos to each recipient=5.3), two of whom maintained pregnancy.

Several steps are involved in the method of the invention. These steps include: synchronization and superovulation, embryo recovery, and embryo transfer. Not all of these steps are necessarily involved in every implementation of the multiple birth goat system. The precise steps and techniques involved depend on use to which the system is being put. In many cases the dwarf goat embryos are manipulated (cloned, microinjected, etc.) prior to transfer to the recipient doe (which may be a standard or dwarf goat).

Synchronization and Superovulation

The goats (standards and Dwarf) can be synchronized and superovulated by any established regime known by those skilled in the art. The following hormonal regime is one example of the methods which can be used. Sponges containing 60 mg of methoxyprogesterone acetate were inserted into the vagina of standard and dwarf goats and left there for 17 days. For three days, starting on day 15 of the sponge treatment, the dwarf goats (embryo donors) received two injections of follicle stimulating hormone (FSH) a day in a decreasing dosage (5 mg, 4 mg, 3 mg, 2 mg, 2 mg, and 2 mg, with 200 I.U. PMSG on day 2). Breeding was achieved by having the buck with the does on day 18 and 19. Alternately the doe can be inseminated artificially. Standard goat recipients were not breed, but were synchronized using the sponges. Lower doses of FSH or pregnant mare serum gonadotropin (PMSG; 400 I.U.) can also be used in the synchronization of the recipients to ensure ovarian response. The embryos are collected and transferred five days following breeding.

Recovery of Embryos

Embryos were recovered and transferred surgically using standard procedures. The goats were fasted 24 hours prior to surgery then given 0.66 mg atropine sulfate. Anaesthesia was induced with intravenous administration of diazepam (1 mg/kg body weight) and ketamine (5 mg/kg). Anaesthesia was maintained with halothane via endotrachial intubation. For morula and blastocyst stage embryos (day 4–6 post insemination) the uterus was exposed and the proximal uterine horn occluded with a Foley catheter (Fr. 10 or 12 for standard does and Fr. 10 for Dwarf does). A Fr. 3½ Tom Cat catheter was inserted at the utero-tubal junction and 10 to 20 ml of media was introduced into the uterus. This fluid was drained by gravity into a sterile receptacle. Both horns of the uterus were treated in the same way. Earlier staged embryos can be recovered in a similar manner by flushing the oviducts (day 1–3 post insemination). Other embryo recovery methods can also be used in the method of the invention.

Embryo Transfer

The dwarf goat embryos were introduced into synchronized recipient standard goats either by a surgical procedure similar to embryo recovery, or by laparoscopic or nonsurgical procedures (Pendleton et al., *Louisiana Agriculture*, 29:6–7, 1986, describes such procedures). In the surgical procedure the exposed uterus was pierced with a needle (18 g) and a Tom Cat catheter carrying the embryos in a minimal amount of media was inserted through the puncture hole and carefully threaded into the uterine horn. The embryos were expelled into the uterine horn and the catheter carefully removed.

Various embryo transfer techniques applicable to diary goats are described by Youngs et al. (Youngs et al., Embryo Transfer in Dairy Goats, in *The Proceedings of the Intl. Goat Production Symposium*, Florida A & M Univ., Tallahassee, Fla., 1990). This reference also describes related techniques including: embryo cyropreservation, embryo splitting, in vitro embryo culture, gene transfer, nuclear transplantation, in vitro fertilization, and embryo sexing. Various embryo transfer techniques applicable to diary goats are described by Youngs et al. (supra). Braun et al. describes useful methods for non-surgical collection of goat embryos. (Braun et al., Non-surgical Embryo Collection in the Dairy Goat, in *The Proceedings of the Intl. Goat Production Symposium*, Florida A & M Univ., Tallahassee, Fla., 1990).

C. Embryo Manipulation

The embryos recovered from the Dwarf embryo donor may be manipulated prior to embryo transfer using the following methods or other methods known to those skilled in the art. In general, any method for the production of transgenic goats can be used in the method of the invention.

Microinjection

Microinjection of the transgene into the pronuclei of zygotes (produced either in vivo or in vitro) is a preferred method for the generation of transgenic animals. The pronuclei can be visualized by differential interference contrast which can be aided by briefly centrifuging the zygotes. DNA solution, for example an expression vector with the casein control element driving expression of the desired transgene, is injected into one of the pronuclei. Injected zygotes can either be transferred surgically to the oviducts of recipients or cultured in vitro until the morula or blastocyst stage for surgical or non-surgical transfer, possibly following embryo biopsy. *Guide to techniques in Mouse Development* (supra) provides detailed descriptions of a wide variety methods which can be used to produce transgenic animals and manipulate embryos. Simons et al. describes examples of the use of microinjection of sheep pronuclei and the production of transgenic sheep which produce human clotting factor IX and $\alpha$1-antitrypsin (*Bio/technology*, 6:179, 1989). Meade et al. (U.S. Pat. No. 4,873,316) describes a microinjection techniques and expression systems suitable for expression of recombinant proteins in mammal's milk.

Ebert et al. (*Bio/technology* 12:699, 1994) describe the induction milk containing of human tissue plasminogen activator from the mammary gland of transgenic goats from a first generation transgenic male. Ebert et al. (supra) also describe a useful method for induction of lactation in males using a hormonal regime. This method permits early assessment of a transgene expressed in the mammary glands, even in males.

Embryo Biopsy

Under some circumstances it is desirable to obtain a few cells from an embryo. The cells can be used to determine the gender of the embryo, determine whether the transgene is present, and assess the structure of the transgene (e.g., whether it has been rearranged). One to a few cells can be removed, preferably at the 16 cell or greater stage, using micro instruments. Genotyped embryos can be transferred to recipients or can be stored frozen for later transfer.

In vitro Development of Oocytes

Keskintepe et al. describe a method for developing morulae in vitro from immature goat oocytes (*Zygote* 2:97, 1994). This method can be used to provide zygotes and embryos for gene manipulation, host embryos for chimera production, unfertilized recipient oocytes for use in nuclear transfer, and embryos and oocytes for use in other techniques.

Expansion of Transgenic Embryos by Chimera Production

Transgenic dwarf goat embryos, including those produced by pronuclear injection, nuclear transfer, or obtained from a transgenic animal, can be split into small sets of cells, preferably 3 to 6 cells, but also as few as one and as many as half of the embryo's cells. Each small set of cells (or each cell) can be injected into an intact host goat embryo or sandwiched between the separated cells of a host goat embryo for the production of chimeric goats. The host embryo can be produced in vivo or in vitro. Dwarf goat embryos are preferred hosts, although standard goat embryos can also be used, particularly where the host cells are directed to placental formation. It can be diploid or tetraploid. By controlling the ratio of injected embryo to host embryo cells, stage of host (younger), ploidy of host (tetraploid) or differentiation of host (trophectoderm) and embryo (inner cell mass), the host embryo can be directed towards placental formation while the transgenic (injected) embryo can be directed towards fetal contribution.

Embryonic Stem Cell Isolation and Culture

Embryonic stems cells (ESC) are very useful in the production of transgenic animals. They can be genetically transformed and then used to form chimeric embryos by blastocyst injection, morula injection, aggregation, or other techniques (see *Guide to Techniques in Mouse Development*, supra). ESC harboring the transgene are incorporated into the germ line and participate in the production of reproductive cells, the offspring produced by the chimeric animals will be transgenic. ESC are have several advantages: 1) they permit increased efficiency of transgenic animal production; 2) they can be transformed in vitro; 3) they can be screened for the presence of the transgene (Robertson, *Biology of Reproduction* 44:238, 1991); and 4) they can be propagated so that one can generate many identical transgenic animals. The use of ESC makes it possible to replace an existing gene with a genetically altered gene by homologous recombination (Thomas et al., *Cell* 51:501, 1987). Pieper et al. (*Nucleic Acids Res.* 20:1259, 1992) describes methods for introducing a transgene into a murine zygote by homologous recombination.

The following references provide information concerning the production of ESC and their use in the production of transgenic animals: Wheeler et al. (*Reprod. Fertil. Dev.* 6:563, 1994); Reed et al. (PCT Application No. PCT/US93/08878); Wheeler (PCT Application No. PCTIUS94/05529); Iannocone (PCT Application No. PCT/US94/09787); and Evans et al (PCT Application No. PCT/GB89/01103).

Dwarf goat ESC can be produced as follows. Dwarf goat embryos, preferably at the blastocyst or younger stages, are cultured after removal of the zona pellucida, either through natural hatching process or mechanical removal, on an appropriate feeder cell line such as embryonic fibroblast feeder layers (mouse, STO, goat, etc.). Embryos attach to the monolayer and proliferate as an undifferentiated cell line (embryonic stem cells). These cells can be propagated as a cell line, stored frozen, or transfected with DNA construct by any of known DNA transfer techniques (i.e., these cells are amenable to all somatic cell manipulations known to one trained in the art). ESC can be derived from morulae (Eistetter, *Dev. Growth and Diff.* 31:276, 1989). ESC can also be isolated from primordial germ cells (Matsui et al., *Cell* 70:841, 1992).

Putative dwarf goat ESC were derived as follows. Morula-staged and/or blastocyst-staged embryos were collected from superovulated dwarf goat does on day 6 (esterus=day 0). The embryos were placed into Embryonic Stem Cell Medium (ESCM; MEM (GIBCO) supplemented with nonessential amino acids, 0.1 mM β-mercaptoethanol, and 15% bovine fetal calf serum (FCS) over a feeder cell layer. In this example the feeder cell layer was mitomicin blocked STO cells (available from the American Type Culture Collection, Rockville, Md.). Alternately, mouse embryonic fibroblastic cells, or goat embryonic fibroblastic cells could be used as a feeder layer.

Over a period of 7 days the embryos hatched from their zonae pellucidae and attached to the feeder layer. After a few days (up to and over 2 weeks) attached cells were removed mechanically by cutting into pieces with sharp edge, glass or metal needle or blade, and lifting off the surface. These pieces were then enzymatically dispersed (using trypsin or protease) into small clumps of cells and replated onto plates of fresh feeder cells. The enzymatic treatment can be omitted and the small pieces passaged directly to the new feeder layer.

After 7 to 14 days the embryonic stem cells colonies were passaged again as described above. This passaging step is repeated as needed. Colonies can be passage while small and undifferentiated or can be allowed to almost reach confluency. Large colonies may have areas of differentiated and undifferentiated cells. Undifferentiated cells can be preferentially removed for continued passage.

ESC can be frozen 10% glycerol and 90% ESCM. ESC lines can be restarted from frozen cells. Frozen cells are thawed rapidly, washed free of cryoprotectant and plated onto fresh feeder layers.

As an alternative culture method, established ESC (after 1 passage) can be plated onto gelatin coated tissue culture plate instead of feeder cell layers. The ESC medium is supplemented with BRL cell conditioned medium (60% BRL conditioned MEM supplemented with 40% ESCM and 0.1 mM β-mercaptoethanol).

The ESC prepared as described above have a large nuclear to cytoplasmic ratio. At high cell numbers, the ESC grow in a flat monolayer with indistinct cellular edges. Colony edge is distinct and smooth. Cell size is less than or equal to 21 μm. When plated as single cells or in small clumps they form a small mound which will later expand to large flat colony as numbers increase. Undifferentiated cells are alkaline phosphate positive and form simple embryoid bodies spontaneously as cell numbers (colony size) increases. Some colonies may spontaneously differentiated into large flat (trophectoderm-like) cells and/or with cells which have morphological characteristics of nerve cells and/or muscle cells.

Embryonic Stem Cell-Chimera Production

Embryonic stem cell, preferrably selected for the appropriate incorporation of a transgene, are injected into a host embryo, preferably when the host embryo is at the morula or blastocyst stage, although injection can occur when the embryo is even younger. The ESC used are preferably from selected colonies which are separated into small clumps of cells (preferably five to fifteen cells) either by mechanical or enzymatic (pronase or trypsin) treatment. These cells would be injected into the blastocoel of blastocyst staged embryos or under the zona into the mass of morula or younger stage host embryos. Alternately, zona free morula (or younger) embryos can be cultured with ESC separated by enzymatic treatment, allowing ESC to be incorporated into the embryo. Host embryos can be in vivo or in vitro produced, diploid or tetraploid. Guide to Techniques in Mouse Development (supra) describes techniques employing ESC in the production of transgenic animals.

Nuclear Transfer for Multiplication of Embryos

Nuclear transfer is an alternative method for propagating transgenic animals. The nuclear donor source can be either a cell taken from a transgenic embryo (following pronuclear injection or derived from a transgenic dam/sire) or a transgenic embryonic stem cell. The cytoplast/host source can be any goat oocyte, in vitro or in vivo matured.

The host oocyte is enucleated (metaphase II chromosomes removed) either by microsurgical or by centrifugation methods. The resulting host cytoplast is activated by any number of means (cold shock, electrical pulse, calcium ionophore—DMAP treatment, ethanol, etc.) prior or post nuclear transfer depending on the cell cycle stage of the donor nucleus. Generally, embryonic cells are transferred to a preactivated cytoplast while the ES cell-cytoplast are activated post transfer and fusion. The donor nuclei are obtained by either mechanical or enzymatic (for example, trypsin, protease) separation of the donor embryo or cell line. The individual cells (karyoplasts) are transferred to the enucleated oocyte (cytoplast) under the surrounding zona pellucida such that there is contact between the plasma membranes of the karyoplast and cytoplast. The karyoplast and cytoplast are fused by any of several methods including but not limited to, electrofusion, PEG, fusogenic proteins or viruses, etc. The new zygote is cultured to an appropriate stage for transfer to a recipient animal or frozen storage. An alternate method to karyoplast/cytoplast fusion is that the donor nucleus can be injected directly into the ooplasm of the enucleated oocyte (Collas et al., *Molecular Reproduction and Development* 38:264, 1994). The new zygotes produced by these nuclear transfer techniques can also be combined with a host embryo (in the manner described above) to produce chimeras. Prather et al. (U.S. Pat. No. 4,994,384) and Massey (U.S. Pat. No. 5,057,420) describe nuclear transfer methods. Tatham et al. (*Biology of Reproduction* 53:1088, 1995) describes additional nuclear transplantation methods.

D. Use of Transgenic Goats

The transgenic dwarf goats produced by the method of the invention can be used to produce useful human theraputic proteins (e.g., human growth hormone) and veterinary therapeutic proteins (e.g., IL-6) in the milk of the dwarf goats. Production of the heterologous protein in a mammal facilitates post-translational modification of the protein and obviates expensive cell culture media used in in vitro methods of protein production. The invention also offers the advantage that the heterologous protein can be produced in large quantities. Transgenic goats can also be used to alter the characteristics of milk.

Transgenic goats can be used for many of the same purposes for which other transgenic animals have been used. The following references describe a variety of uses for transgenic animals: Sarvetnick et al. (PCT Application No. PCT/US94/04708); Bjursell et al. (PCT Application No. PCT/SE93/00515); Lonberg (PCT Application No. PCT/US94/04580); and Abraham et al. (PCT Applicaton No. PCT/GB94/00569).

For example, expression of an appropriate transgene can cause alterations in the protein, lipid, or carbohydrate content of the milk. Useful milk products, such as those having a reduced lactose content, can readily be produced. In addition, where the transgene expresses β-galactosidase derived from *Aspergillus niger*, the enzyme is particularly useful for hydrolyzing lactose at an acidic pH (at pH 3–4). Accordingly, a sample of milk including this enzyme is particularly useful for reducing the lactose content of a second sample of milk by simply mixing the two milk samples together.

Where the heterologous enzyme is an aspartic protease, the milk is particularly useful for producing cheese. Such proteases decrease the time required for milk to be clotted by rennet. Aspartic proteases can also increase the yield of cheese. The expression of a bovine β-casein in milk can also improve cheese yields. In addition, the production of bovine β-casein or other heterologous proteins (e.g., lactoferrin or lysozyme) in milk can increase the nutritional value of the milk.

Because heterologous enzymes can be tethered to the mammary epithelial cell membrane, the invention also enables the production of modified milk, while decreasing the concern that such milk contains heterologous enzymes. Tethering enzymes to the mammary epithelial cell membrane also decreases the demand placed on the cell's synthetic machinery, since the enzyme can act on components of the milk without being secreted into the milk.

E. Transgenes

Useful promoters for the expression of transgenes in the mammary tissue include promoters which naturally drive the expression of mammary-specific. For example, the αS1-casein promoters, αS2-casein promoters, β-casein promoters, κ-casein promoters, β-lactoglobulin promoters, whey acidic protein promoters, and α-lactalbumin promoters can be used. If desired, the promoter can be operably linked to one or more enhancer elements such that the enhancer element(s) increases transcription of the gene encoding the heterologous gene product.

The following references describe genes and expression control regions useful in the construction of transgenes in a variety of livestock: Groenen et al. (*Livestock Production Science* 38:61, 1994); Wilmut et al. (*Experientia* 47:905, 1991); Pursel et al. (*J. Animal Sci.* 71(suppl. 3):10, 1993); Clark et al. (U.S. Pat. No. 5,322,775); and Bleck et al. (PCT Application No. PCT/US92/06549). Expression constructs and genes used in livestock other than goats can, if required, be adapted for use in goats. Hurwitz et al. (PCT Application No. PCT/US/06300) describes expression constructs suitable for expression of a heterologous protein in the milk of a goat.

Preferably, the genetic construct (i.e., plasmid) also includes a transcription termination region. Useful termination regions include a polyadenylation signal and the 3'-end of the gene from which the promoter region of the genetic construct was derived. Other useful transcription termination regions include termination regions which are known to affect mRNA stability, such as those derived from the bovine growth hormone gene, globin genes, the SV40 early region or milk protein genes.

Optionally, the linear or circular genetic construct includes an intron which can increase the level of expression of the heterologous gene. Generally, the intron should be placed between the transcription initiation site and the translational start codon; 3' of the translational stop codon; or within the coding region of the gene encoding the heterologous protein. The intron should include a 5' splice site (i.e., a donor site), a 3' splice site (i.e., an acceptor site), and preferably includes at least 100 nucleotides between the two sites. Particularly useful introns are those which are naturally found in genes of ruminants (e.g., genes encoding caseins).

Heterologous Gene Products

Practically any heterologus protein can be produced in a transgenic dwarf goat. Particularly useful heterologous proteins include those which are of therapeutic value to humans or animals (e.g., htPA, hGH, and IL-6). Other particularly useful proteins include those which increase the nutritional value of the milk (e.g., β-casein and lactoferrin). Many genes encoding these and other useful proteins have been identified and cloned, allowing them to be readily subcloned for use in the production of transgenic dwarf goats.

Other particularly useful heterologous proteins include those which are valuable in food science. Among the useful proteins are those which possess an enzymatic activity directed toward a component of milk; such enzymes can be used to alter the lipid, protein, or carbohydrate content of the milk. For example, β-galactosidase can be produced with the invention to produce milk with a reduced lactose level. Genes encoding β-galactosidase can be derived from any of a number of organisms, including *Aspergillus niger*, (Kumar et al., 1992, *Bio/technology* 10:82); *Homo sapiens* (Oshima et al., 1988, *Biochem. Biophys. Res. Comm.* 157:238); *Kluyveromyces lactis* (U.S. Pat. No. 5,047,340; Sreekrishna and Dickson, 1985, *Proc. Natl. Acad Sci.* 82:7909; and Poch et al., 1992, *Gene* 118:55); *Lactobacillus bulgaricus* (Schmidt et al., 1989, *J. Bacteriology* 171:625).

Useful proteins include: cytokines, aspartic proteases, lysozyme, stearyl-CoA desaturase, lipases, galactosyltransferase, blood clotting proteins, protein C, α1-antitrypsin, urokinase plasminogen activator, human serum albumin, cystic fibrosis transmembrane conductance regulator, gamma-interferon, human CD4, growth factors, peptide hormones, oncoproteins, tumor suppressor proteins, milk proteins, hormone receptors, translation factors, and transcription factors.

If desired, the gene encoding the heterologous protein can be mutated. Particularly useful mutations include mutations in the 5'- or 3'-untranslated regions of the gene, because such mutations may improve expression of the gene encoding the heterologous protein. Other useful mutations or deletions are those which increase secretion of the protein from the cell or inhibit retention of the protein inside the cell. For example, sequences encoding endoplasmic reticulum retention signals or other sorting inhibitory signals are preferably deleted from the genetic construct or mutated to be non-functional. In addition, truncated versions of naturally-occurring proteins can be used in the invention, provided that the truncated protein possesses a useful biological activity.

Each heterologous protein produced according to the invention should be bonded to a signal peptide if the protein is to be secreted from the mammary epithelial cell. The signal peptide can be a naturally-occurring component of the heterologous protein (e.g., the signal peptide of human placental β-galactosidase). Where the heterologous protein is not naturally a secreted protein, if secretion is desired, the genetic construct should be assembled such that a signal peptide is bonded to the heterologous protein so that the signal peptide directs secretion of the protein from the cell. Useful signal peptides can be derived from genes such as casein genes, the gene for human alkaline phosphatase, or the gene for melittin.

Tethered Enymes

Where the genetic construct encodes an enzyme to be tethered to the epithelial cell membrane, the genetic construct can include a sequence encoding a membrane-associated polypeptide. For example, the genetic construct can include a sequence derived from β-1,4-galactosyltransferase (see, e.g., Masri et al., 1988, *Biochem. Biophys. Res. Comm.* 175:657–663), lactase-phlorizin hydrolase (see, e.g., Mantei et al., 1988, *EMBO J.* 7:2705–2713), the thy-1 protein (see, e.g., Brown et al., 1989, *Science*, 245:1499–1501), or the sodium/glucose transporter (see e.g., Kong et al., 1993, *FEBS Letters* 333:14).

Tethering an enzyme to the cell membrane allows the enzyme to be active on a component of milk, while inhibiting secretion of the enzyme into milk obtained from the mammal. Tethering the enzyme to the cell membrane can decrease the amount of heterologous enzyme that must be synthesized for modification of the milk components. While secreted enzymes remain in contact with milk in the bovine duct for approximately 12 hours before they are removed with the milk, the time span for tethered enzymes is limited only by the natural turnover of the epithelial cell membrane. Because the enzyme remains in the duct where it can act on milk produced over a long period of time, the cell may not need to synthesize as much of the heterologous enzyme as would be required if the heterologous enzyme were secreted. In addition, while milk obtained from such mammals can be modified as desired (e.g., to have a reduced lactose content), tethering the enzyme to the cell membrane decreases the concern that the modified milk contains an undesired heterologous enzyme.

Antisense Oligonucleotides

Where the genetic construct encodes an antisense oligonucleotide for inhibiting gene expression, the construct is engineered to produce an oligonucleotide which hybridizes to DNA or mRNA of the gene. Generally, this aspect of the invention can be practiced using art-known antisense strategies. The DNA sequences of a number of mammary epithelial cell genes are known. Appropriate targets include, without limitation, genes encoding a β-lactoglobulin (see e.g., Ivanov et al., 1988; *J. Biol. Chem.* 369:425–429, and Silva et al., 1990, *Nucleic Acid Res.* 18:3015), an acetyl CoA carboxylase, a galactosyltransferase (Shaper et al., 1986, *Proc. Natl. Acad Sci.* 83: 1573–1577; Masibay et al., 1989, *Proc. Natl. Acad Sci.* 86: 5733–5737; Masri et al., 1988, *Biochem. Biophys. Res. Comm.* 175:657–663), and an α-lactalbumin (Vilotte et al., 1987, *Biochimie* 69:609–620). Thus, those skilled in molecular biology will be able to design a genetic construct encoding an antisense oligonucleotide of a suitable sequence and length. Preferably, the antisense oligonucleotide is between 5 and 1,000 nucleotides in length (more preferably 10 to 500 nucleotides).

Ribozymes

The gene transfer method of the invention can also be used to deliver genetic constructs encoding ribozymes to the mammary epithelial cells. Conventional strategies can be used in the design of genetic constructs encoding ribozymes. Appropriate target nucleic acids include, without limitation, those which encode β-lactoglobulin, acetyl CoA carboxylase, galactosyltransferase, and α-lactalbumin.

Genetic Knockouts

Using embryonic stem cell technology, one can knock out a selected gene.

Isolation and Characterization of Genetic Constructs

The genetic constructs useful in the invention can be prepared using conventional techniques for DNA isolation. If desired, DNA quality can be assessed with standard methods, such as measuring optical density or analyzing the DNA by electrophoresis. Preferably, the DNA is endotoxin free, and suitable methods include those which have been approved for purifying DNA for use in humans (e.g., the use of a Qiagen DNA extraction kit followed by the use of an endotoxin elimination kit). If desired, the genetic constructs can be further characterized by sequencing the DNA molecules, particularly at junctions formed by the ligation of two DNA molecules. The creation of partial restriction maps from the genetic constructs can provide information regarding the orientation of the gene encoding the heterologous protein relative to the other components of the construct.

What is claimed is:

1. A method for producing a transgenic dwarf goat whose somatic and germ cells comprise a transgene expressed in the mammary tissue of the transgenic dwarf goat, said method comprising:

(a) introducing a transgene into a zygote or embryo of a dwarf goat, wherein said transgene comprises a DNA sequence encoding a protein in operable linkage with a promoter functional in mammary secretory cells, (b) transplanting said zygote or embryo into a pseudopregnant goat, (c) allowing said zygote or embryo to develop to term, and (d) identifying at least one dwarf goat, wherein expression of said transgene results in the production and secretion of a protein encoded by said DNA in the mammary tissue of said dwarf goat.

2. The method of claim 1 further comprising breeding said dwarf goat to produce a transgenic dwarf goat, wherein expression of said transgene results in the production and secretion of a protein encoded by said DNA in the mammary tissue of said dwarf goat.

3. The method of claim 1, wherein said introducing said transgene into said zygote is by microinjection.

4. The method of claim 1 wherein said pseudopregnant goat is a non-dwarf goat.

5. The method of claim 4, wherein at least 4 zygotes are transplanted into said pseudopregnant non-dwarf goat.

6. The method of claim 1 wherein said pseudopregnant goat is a dwarf goat.

* * * * *